(12) United States Patent
Bonsignore (10) Patent No.: US 8,562,666 B2
(45) Date of Patent: Oct. 22, 2013

(54) INTRALUMINAL MEDICAL DEVICE WITH NESTED INTERLOCKING SEGMENTS

(75) Inventor: Craig Bonsignore, Pleasanton, CA (US)

(73) Assignee: Nitinol Development Corporation

( * ) Notice: Subject to any disclaimer, the term of this patent is extended or adjusted under 35 U.S.C. 154(b) by 910 days.

(21) Appl. No.: 11/237,574

(22) Filed: Sep. 28, 2005

(65) Prior Publication Data

US 2007/0073373 A1    Mar. 29, 2007

(51) Int. Cl.
    *A61F 2/06*    (2013.01)
(52) U.S. Cl.
    USPC ............................ 623/1.15; 623/1.11; 623/1.2
(58) Field of Classification Search
    USPC .................. 623/1.18, 1.2, 1.11, 1.15–1.16
    See application file for complete search history.

(56) References Cited

U.S. PATENT DOCUMENTS

| | | | |
|---|---|---|---|
| 4,655,771 A | 4/1987 | Wallsten | |
| 4,733,665 A | 3/1988 | Palmaz | |
| 6,251,134 B1 * | 6/2001 | Alt et al. ..................... | 623/1.16 |
| 7,175,654 B2 | 2/2007 | Bonsignore et al. | |
| 2004/0093063 A1 * | 5/2004 | Wright et al. ................ | 623/1.12 |
| 2004/0186551 A1 | 9/2004 | Kao et al. | |
| 2004/0243217 A1 * | 12/2004 | Andersen et al. ............ | 623/1.15 |
| 2005/0055080 A1 | 3/2005 | Istephanous et al. | |
| 2005/0090893 A1 | 4/2005 | Kavteladze et al. | |
| 2007/0032857 A1 * | 2/2007 | Schmid et al. ............... | 623/1.16 |

FOREIGN PATENT DOCUMENTS

| | | |
|---|---|---|
| EP | 1000590 A1 | 5/2000 |
| EP | 1369098 | 12/2003 |
| EP | 1415616 A1 | 6/2004 |
| EP | 1523959 A2 | 4/2005 |
| WO | WO 03022178 A1 * | 3/2003 |

OTHER PUBLICATIONS

European Search Report dated Mar. 5, 2007 for EP Application No. EP 06 25 5015.

* cited by examiner

*Primary Examiner* — Gary Jackson
*Assistant Examiner* — Diane Yabut (57) ABSTRACT

The invention is a medical device having nested interlocking axially adjacent segments that remain interlocked during delivery. The medical device is a stent in which the nested interlocked axially adjacent segments provide increased control and stability of the stent during delivery and increased vessel support when deployed. A series of repeating cells comprise a segment. Each cell comprises a protrusion and a radially and circumferentially adjacent receptacle. The protrusion from at least one cell in a segment interlocks with the receptacle of an axially adjacent segment to form the stent. The protrusions remain coupled with a corresponding receptacle during delivery of the stent to the intended treatment site, and can remain engaged thereafter, or can disengage from the corresponding receptacle after full deployment of the stent.

16 Claims, 7 Drawing Sheets

INTRALUMINAL MEDICAL DEVICE WITH NESTED INTERLOCKING SEGMENTS

BACKGROUND OF THE INVENTION

1. Field of the Invention

The invention relates to intraluminal medical devices. More particularly, the invention relates to stents having nested interlocking segments that provide increased stability by remaining interlocked during delivery, and that provide enhanced vascular support, while maximizing fatigue durability of the implant.

2. Related Art

Percutaneous transluminal angioplasty (PTA) is a therapeutic medical procedure used to increase blood flow through an artery. In this procedure, an angioplasty balloon is inflated within the stenosed vessel, or body passageway, in order to shear and disrupt the wall components of the vessel to obtain an enlarged lumen. A dissection "flap" of underlying tissue can occur, however, which can undesirably fold into and close off the lumen. Immediate corrective surgery becomes necessary as a result.

More recently, transluminal prosthesis, such as stents, have been used for implantation in blood vessels, biliary ducts, or other similar organs of a patient in order to open, dilate or maintain the patency thereof. An example of such a stent is given in U.S. Pat. No. 4,733,665 to Palmaz. Such stents are often referred to as balloon expandable stents. A balloon expandable stent is typically made from a solid tube of stainless steel having a series of cuts made therein. The stent has a first smaller diameter, permitting the stent to be crimped onto a balloon catheter for delivery through the human vasculature to an intended treatment site. The stent also has a second, expanded diameter, that is achieved by the application of a radially, outward directed force by the balloon catheter from the interior of the tubular shaped stent when located at the intended treatment site.

Such balloon stents are often impractical for use in some vessels, such as the carotid artery. The carotid artery is easily accessible and close to the surface of a patient's skin. Thus, emplacement of a balloon expandable stent in such a vessel poses severy injury risks to a patient through even day-to-day activities, particularly where a force to the patient's neck could result in collapse of the stent within the vessel. Self-epanding stents have thus been devised in part to address these risks, wherein the self-expanding stent will recover its expanded state after being temporarily crushed by a force applied to a patient's neck or the like.

One type of self-expanding stent is disclosed in U.S. Pat. No. 4,655,771. The stent disclosed in U.S. Pat. No. 4,655,771 has a radially and axially flexible, elastic tubular body with a pre-determined diameter that is variable under axial movement of the ends of the body relative to each other and which is composed of a plurality of individually rigid but flexible and elastic thread elements defining a radially self-expanding helix. This type of stent is known in the art as a "braided stent" and is so designated herein. Placement of such braided stents in a body vessel can be achieved by a device which comprises an outer catheter for holding the stent at its distal end, and an inner piston which pushes the stent forward once it is in position.

Braided stents have many disadvantages, however, including insufficient radial strength to effectively hold open a diseased vessel. In addition, the plurality of wires or fibers comprising a braided stent become dangerous if separated from the body of the stent as they could pierce through the vessel. Tube-cut stents made from alloys having shape memory and/or superelastic characteristics have thus been developed to address some of the concerns posed by braided stents.

The shape memory characteristics allow the devices to be deformed to facilitate insertion into a body lumen or cavity, whereafter resumption of the original form of the stent occurs when subjected to sufficient heat from the patient's body, for example. Superelastic characteristics, on the other hand, generally allow the stent to be deformed and restrained in the deformed condition to facilitate insertion of the stent into the patient's body, wherein the deformation of the stent causes a phase transformation in the materials comprising the stent. Once within the body lumen of the patient, the restraint on the superelastic stent is removed and the superelastic stent returns to its original un-deformed state.

Alloys having shape memory/superelastic characteristics generally have at least two phases. These phases are a martensite phase, which has a relatively low tensile strength and which is stable at relatively low temperatures, and an austentite phase, which has a relatively high tensile strength and which is stable at temperatures higher than the martensite phase.

Shape memory characteristics are imparted to an alloy by heating the alloy to a temperature above which the transformation from the martensite phase to the austenite phase is complete, i.e., a temperature above which the austenite phase is stable (the $A_f$ temperature). The shape of the metal during this heat treatment is the shape "remembered". The heat-treated alloy is cooled to a temperature at which the martensite phase is stable, causing the austenite phase to transform to the martensite phase. The alloy in the martensite phase is then plastically deformed, e.g., to facilitate the entry thereof into a patient's body. Subsequent heating of the deformed martensite phase to a temperature above the martensite to austenite transformation temperature causes the deformed martensite phase to transform to the austenite phase, and during this phase transformation the alloy reverts back to its original shape if unrestrained. If restrained, the metal will remain martensitic until the restraint is removed.

Methods of using the shape memory characteristics of these alloys in medical devices intended to be placed within a patient's body present operational difficulties. For example, with shape memory alloys having a stable martensite temperature below body temperature, it is frequently difficult to maintain the temperature of the medical device containing such an alloy sufficiently below body temperature to prevent the transformation of the martensite phase to the austenite phase when the device was being inserted into a patient's body. With intravascular devices formed of shape memory alloys having martensite-to-austenite transformation temperatures well above body temperature, the devices can be introduced into a patient's body with little or no problem, but they must be heated to the martensite-to-austenite transformation temperature which is frequently high enough to cause tissue damage.

When stress is applied to a specimen of an alloy or metal such as Nitinol exhibiting superelastic characteristics at a temperature above which the austenite is stable (i.e., the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain, but with little or no corresponding increases in stress. The strain increases while the stress remains essentially constant until the transformation of the austenite phase to the martensite phase is complete. Thereafter, further increases in stress are necessary to cause further deformation. The martensitic alloy or metal first deforms elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e., there is significant recovery in strain with only negligible corresponding stress reduction. After the transformation back to the austenite phase is complete, further stress reduction results in elastic strain reduction. This ability to incur significant strain at relatively constant stress upon the application of a load, and to recover from the deformation upon the removal of the load, is commonly referred to as superelasticity or pseudoelasticity. It is this property of the material which makes it useful in manufacturing tube cut self-expanding stents.

The compressive forces associated with stent loading and deployment can pose concerns with respect to self-expanding stents. In stent designs having periodically positioned bridges, for example, the resulting gaps between unconnected loops may be disadvantageous. In both the loading and the deployment thereof, the stent is constrained to a small diameter and subjected to high compressive axial forces. These forces are transmitted axially through the stent by the connecting bridges and may cause undesirable buckling or compression of the adjacent loops in the areas where the loops are not connected by bridges.

Other concerns with self-expanding stents include reduced radiopacity, often resulting in the attachment of markers to the stent. The attached markers tend to increase the profile of the stent, and can dislodge from the stent or otherwise compromise the performance of the stent.

A still further concern is the transmission of forces between interconnected elements of a stent. Conventional vascular stents tend to comprise a series of ring-like radially expandable structural members that are axially connected by bridging elements. When a stent is subjected to in vivo bending, stretching or compression, its ring-like structural members distribute themselves accordingly, thus allowing the structure to conform to its vascular surroundings. These loading conditions cause the ring-like structural members to change their relative axial positions. The bridging elements help to constrain the ring-like structural members and therefore propagate strain between the ring-like structural members. The axial and radial expansion of the otherwise constrained stent, and the bending of the stent, that occurs during delivery and deployment, often renders conventional interconnected stents susceptible to fatigue fractures. Physiologic dynamics within the body of a patient also contribute to fatigue fractures of conventional stents.

Even where connected strut segments have been designed to disconnect upon deployment in order to minimize the occurrence of fatigue fractures, such as in co-pending U.S. patent application Ser. No. 10/687,143, filed Oct. 18, 2003, of common assignment herewith, such stents can prove unstable and susceptible to tipping or rotation within a vessel, particularly during delivery. Moreover, where the L/D ratio, i.e., the ratio of a expanded strut length L to an expanded diameter D, is greater than one due to a length L greater than a diameter D, for example, then the stent tends to be weaker and intended vessel support tends to be compromised. The weaker stent can be even more susceptible to fatigue fractures or other strain induced irregularities, while the longer stent segment lengths L result in larger gaps between structural components of the stent, which compromises vessel support. On the other hand, where the L/D ratio approaches zero, particularly where L approaches zero, then uniform and predictable positioning of the various segments comprising a stent is compromised. For example, where the length L of a protrusion approaches zero, then segments tend to de-couple before becoming firmly opposed to the lumen of the intended blood vessel. As a result, unpredictable propelling of the segments from the delivery device can occur.

In view of the above, a need exists for a stent having interlocked strut segments that remain connected during delivery until after deployment is effected so as to provide a more stable emplacement of the stent within a vessel or other body passageway. A need further exists to provide a stent having improved vessel support while minimizing fatigue fracture tendencies or other strain induced irregularities of the stent during loading, delivery and deployment thereof.

SUMMARY OF THE INVENTION

Various aspects of the systems and methods of the invention comprise an intraluminal medical device having nested interlocking segments that remain interlocked when delivered to an intended treatment site. The medical device is preferably a stent wherein nested interlocked segments provide increased stability of the stent during delivery thereof to the intended treatment site. Ideally the stent further provides increased vascular support to a vessel in which the stent is emplaced.

In a preferred embodiment, the stent comprises multiple, self-expanding segments axially adjacent one another. Each segment is further comprised of a series of repeating cells radially and circumferentially aligned with one another to comprise the segments and aligned with axially adjacent cells to comprise the stent. Each cell further comprises a protrusion and at least one receptacle radially and circumferentially adjacent one another. A predetermined number of protrusions from cells in each segment is received by a corresponding receptacle in an axially adjacent segment. The stent thus comprises at least one axially interconnected protrusion and receptacle, although it is preferable to have more than one interconnected protrusion and receptacle. The protrusions can include radiopaque markers to enhance fluoroscopic, or other, visualization.

In some embodiments, the at least one protrusion from cells of each segment nests within the corresponding receptacle of an axially adjacent segment during delivery of the stent to the intended treatment site. The protrusions uncouple from the respective receptacles upon expansion of the stent when full deployment is effected. In other embodiments, the protrusions remains engaged with the respective receptacles as and after deployment is effected. By lengthening the interlocked components of the stent segments, the coupling of the interlocked components is maintained longer, thereby minimizing undesirable tipping or other rotation of the stent during delivery and minimizing the likelihood of undesirable propelling of the segments during delivery. Further, to the extent that the nesting of the interlocked components exists after deployment of the stent, such nesting enhances vascular support to the vessel even where uncoupling of the protrusions and receptacles occurs.

In still other embodiments, the stent is comprised of a balloon expandable stent that is otherwise generally the same as the self-expanding stent embodiment described herein. Each segment of the balloon expandable stent likewise comprises a series of cells, at least one cell of the series of cells having at least one protrusion coupled with a corresponding receptacle provided from a cell of an axially adjacent stent segment. The nesting of segments via receipt of the protrusions in a corresponding receptacle of an axially adjacent segment during delivery of the balloon expandable stent to the intended treatment site similarly helps to stabilize the stent until expansion thereof is effected by the balloon in this instance. As before, the at least one protrusion of each cell may disengage from the corresponding axially adjacent receptacle after full deployment of the stent is effected, or may remain engaged with the receptacle after deployment is effected. Vascular support is enhanced by the length of the components comprising the segments.

Stents are commonly placed in wide variety of bodily lumens and vascular segments, many of which are routinely subject to a variety of motions and deformations. Often, these deformations are cyclic in nature. Examples include the pulsatile cycle of the cardiovascular system, peristaltic cycle of the gastrointestinal system, breathing cycle of the respiratory system, and gait cycle associated with walking. These cyclic bodily motions result in cyclic loading of many lumens and vessels into which stents are placed. This cyclic loading results in cyclic deformation of these lumens and vessels in a variety of directions. The direction and nature of deformation is a function of the nature of the loading, as well as physiological and anatomical constraints associated with the vessel or lumen. For example, the pulsatile cycle causes cyclic changes in the internal pressure of a vessel, thus resulting in cyclic changes in vessel diameter. Furthermore, the magnitude of this change in diameter is associated with the mechanical and structural properties of the vessel and surrounding tissue; the magnitude of diameter change in a highly calcified diseased vessel will be less than that of a healthy elastic vessel. In another example, flexion of the knee and/or hip cause changes in the length and shape of the vessels of the leg. The magnitude and direction of such vascular deformation is strongly influenced by surrounding elements of the musculo-skeletal system, including muscles, tendons, bones, and joints, all of which may be in motion as the leg is flexed. Similar examples exist throughout the body, including the coronary arteries flexing with the beating of the heart, and renal arteries flexing during the breathing cycle.

The nature and direction of lumen or vessel deformation may be characterized in several dimensions. For a given physical state $P_1$, consider a given vessel or lumen segment $S_1$ assumes a shape in three dimensional space, and that shape has a integral length $L_1$. For simplicity, we shall assume that $S_1$ is in the form of a straight line, such that $L_1$ is simply the distance from the beginning of the segment of interest to the end of that segment of interest. With this simplification, we can also define the radius of curvature of segment $S_1$ as $R_1=\infty$. Further, we can note that in state $P_1$, the change in rotational angle from the beginning to the end of $S_1$ is defined as $\theta_1=0$. Now, consider physical state $P_2$, which may be considered to be the opposing cyclic extreme of physical state $P_1$. For example, $P_1$ and $P_2$ may represent systolic and diastolic pressures of the circulatory system, states of leg extension and flexion, or any such instances of dynamic states. Under physical state $P_2$, vessel $S_1$ assumes a new shape $S_2$. In physical state $P_2$, segment $S_2$ may experience a change in integral length $\Delta L$ to assume a new length $L_2$. If $L_2>L_1$, the vessel or lumen may now assume a state of relatively greater tension, while if $L_2<L_1$, it may assume a stent of compression. Considering the constraints associated with $S_2$, assuming a state of compression may cause the segment to bend, kink, or buckle. In such a case, the segment $S_1$ may now experience a change in radius of curvature $\Delta R$ such that $R_2<R_1$. Increasing the compressive magnitude of $\Delta L$ may result in changes in the radius of curvature $\Delta R$, with $R_2<R_1$. In fact, it is likely that in such cases, segment $S_2$ may experience multiple local radii of curvature $R_{2a}$, $R_{2b}$, etc, along the length of the segment. Furthermore, in physical state $P_2$, the segment may experience a change in rotational angle between the beginning and end of $S_2$ described as $\Delta\theta$, with $\theta_2>\theta_1$.

To this point, the absolute length $L_1$ of the segment of interest $S_1$ has been considered arbitrary. This length is, however, an important factor in determining the magnitude of changes in deformations $\Delta L$, $\Delta R$, and $\Delta\theta$. If $L_1$ is relatively short (for example, $L_1 \cong D_v$, where $D_v$ is the diameter of the vessel or lumen), it is likely that the segment can be well approximated by a straight line, $\Delta R$ may be well represented by a simple single radius of curvature, and $\Delta\theta$ may be representative of a uniform amount of twist across the length of the segment. As the length of the segment increases (for example $L_1 >> D_v$), non-uniformities along the length of the segment become more probable. The segment is likely to be less well approximated by a straight line, it may be subject to local areas of length change of varying magnitude and direction, multiple local radii become more probable, and likelihood of multiple local twists along the length of the segment is increased. In short, the dynamic complexity of a given segment is likely to increase significantly as the length of that segment increases.

Stents have been successfully implanted throughout the human vascular and non-vascular system. Given the success of stenting short, focal segments, clinical practice has evolved to treat segments of increasing length. While early coronary stents were commonly 15 mm in length, today it is not uncommon to place multiple 40 mm stents within a single coronary artery. Early peripheral vascular stents were 40 mm in length, and today it is not uncommon to place multiple stents>100 mm in a single vessel. These trends to treat ever longer and more diffuse disease create substantial challenges in stent design, particularly in designing stents to withstand the cyclic deformations of the segments in which they are placed.

As a structure is repeatedly loaded and unloaded, stresses and strains within that structure change accordingly. If the cyclic change in stress and strain at any point within the structure exceeds a threshold (known as the endurance limit), the structure may experience fatigue induced cracks and/or fractures after a number of cycles. The term "fatigue durability" describes a structure's ability to withstand cyclic loading and deformation. The fatigue durability is determined by two general categories of parameters: (1) those intrinsic to the structure, including the geometry and dimensions of the structure, and material properties (including the endurance limit), and (2) those extrinsic to the structure. Such extrinsic parameters are often described as the "loading conditions" or the "duty cycle," and include such factors as the magnitude and direction of such deformations as $\Delta L$, $\Delta R$, and $\Delta\theta$ described above.

Considering the prevailing trends to place stents in ever longer segments, the extrinsic drivers of structural fatigue are becoming ever more severe. Designers of implants have no influence on the increasingly demanding duty cycle faced by stents implanted in long segments. Consequently, implant design must focus upon the intrinsic design parameters to enhance fatigue durability.

Conventional stents are often comprised of a series of rings periodically connected by bridging elements to form a continuous structure. Such conventional stents may be comprised of dozens of such rings, and reach lengths well in excess of 100 mm. As noted above, it is not uncommon to implant two or more of these structures in series in a single segment, typically overlapping adjacent stent by several millimeters. In such a case, $L_1$ may be in excess of 200 mm. With such a long length, $\Delta L$ may be great, there may be multiple local radii $\Delta R$, and various local twists $\Delta \theta$ throughout the segment.

Typically, the axial length of each individual ring of a conventional stent structure $L_r$ is $\leq D_v$. This allows the structure to conform to any local changes in curvature or diameter within the stent, while maintaining adequate scaffolding and apposition. These individual rings are typically connected to adjacent rings by one or more bridging elements to form a continuous structure.

Now consider implanting such a conventional stent structure within segment $S_1$. As physical state $P_1$ changes to physical state $P_2$, the segment with an initial shape $S_1$ will now transform to $S_{2s}$. Note that shape $S_{2s}$ is not necessarily the same as shape $S_2$, as in this case, the presence of the stent adds to the physiological and anatomical constraints experienced by the segment. Under these conditions, the stented segment experiences deflections $\Delta L_s$, $\Delta R_s$, and $\Delta \theta_s$. These deflections are likely to be nonuniform throughout the segment, and the stent structure will locally accommodate these deflections as the design allows.

With a conventional stent structure, each ring will change its shape according to the local deflections experienced in association with vessel deflections described above. In addition, each ring must accommodate the deflections experienced by adjacent rings, as these rings are axially connected by one or more bridging elements. With such bridging elements in place, any change in length $\Delta L$, propagates through the stent, placing the structure in tension or compression to the same extent $\Delta L_s$. Similarly, $\Delta R_s$, and $\Delta \theta_s$ propagate through the length of the conventional stent structure via the bridging elements.

With a nested interlocking stent structure as described herein, however, adjacent rings become decoupled upon expansion. This discontinuous structure provides important intrinsic advantages to improve fatigue durability. To illustrate this advantage, one may consider loading state $P_2$, wherein the segment of interest is placed in pure tension. In this case, the unstented segment is stretched, such that $L_{2s} > L_1$. The advantages of a discontinuous stent structure are illustrated in the following example by comparison to a continuous stent structure places in a vessel experiencing deflection resulting from this loading state $P_2$.

Considering first a continuous stent structure, it is evident that $L_{2s,c} < L_2$. The continuous stent structure axially stiffens the stented segment, thus preventing it from fully stretching to $L_2$, the extent of stretch in absence of a stent. $L_{2s,c} > L_1$, however, indicating that the stent structure is experiencing axial tension. Given this cyclic axial deformation $\Delta L_{s,c}$, the stent structure experiences a cyclic deformation and cyclic strain, and is thus subject to fatigue risk as this cyclic strain approaches the endurance limit.

Considering next a discontinuous stent structure, it is evident that $L_{2s,d} \leq L_2$. In some cases $L_{2s,d} \cong L_2$, and in general $L_{2s,d} > L_{2s,c}$. Without bridging elements to connect individual rings, the rings are free to separate from each other without experiencing any constraints from attachment to adjacent structures. Because each ring is axially independent from adjacent structures, axial deformation of the vessel does not translate into deformation or strain within the individual structures. While the discontinuous stent segment experiences greater overall length change ($\Delta L_{s,d} > \Delta L_{s,c}$), the individual discontinuous members within the segments experience less cyclic strain, and thus improved fatigue durability relative to corresponding members of a connected conventional stent structure. The extension of these principles to general cases of $\Delta L$, $\Delta R$, and $\Delta \theta$, and corresponding advantages of discontinuous structures should be readily apparent to those skilled in the art.

Furthermore, the independent and unconnected nature of a discontinuous stent structure allows the shape of the stented segment $S_{2s}$ to more closely approximate the shape of the unstented segment $S_2$. A conventionally continuous stent structure can not easily accommodate abrupt localized changes in loading or deformation within its length because its bridging elements propagate these local effects to adjacent structures. A discontinuous stented segment allows local effects to remain local, as bridging elements are not present to axially transfer loads or deformations between rings. This behavior beneficially allows preservation of the segment's natural state of deflection, thus improving healing and durability of clinical outcomes.

Finally, in addition to fatigue durability advantages described above, a discontinuous nested interlocking stent system offers natural advantages of convenience and utility when treating segments of increasing length. Conventional continuous stents are typically manufactured in a limited number of lengths, forcing a clinician to compromise by over or under compensating on the stented length. Commonly, clinicians are forced to use multiple stents in series, undesirably overlapping them to some extent to insure against leaving an unsupported gap. A system of nested interlocking discontinuous stent rings offers advantages in that the stented length can be determined by the clinician in-situ, with a resolution equal to the length of a single individual segment. This eliminates the disadvantages of under or over estimating stent length, and also eliminates disadvantages associated with overlapping conventional continuous stents.

The above and other features of the invention, including various novel details of construction and combinations of parts, will now be more particularly described with reference to the accompanying drawings and claims. It will be understood that the various exemplary embodiments of the invention described herein are shown by way of illustration only and not as a limitation thereof. The principles and features of this invention may be employed in various alternative embodiments without departing from the scope of the invention.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE INVENTION

Figure 1:
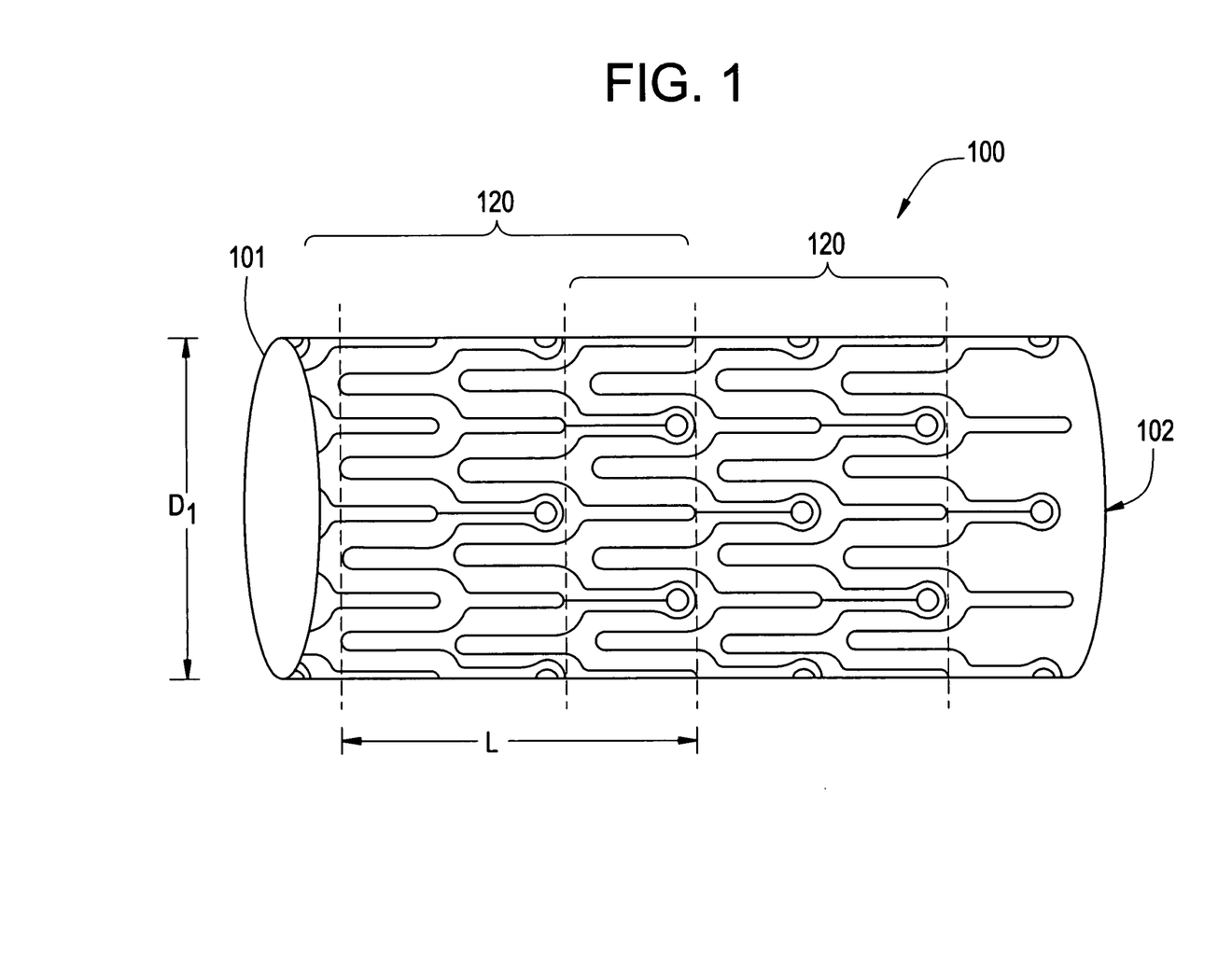
FIG. 1 illustrates a schematic view of an exemplary self-expanding stent with nested interlocking stent segments in accordance with the invention.

FIG. 1 illustrates a schematic view of a stent 100 according to one embodiment of the invention. Unless otherwise indicated, the length L is the length of a segment, for example, segment 120, of the stent 100 in its expanded state, whereas diameter D is the diameter of the stent 100, wherein $D_1$ is the diameter of the stent in its constrained state and $D_2$ is the diameter of the stent in its expanded state. As referenced herein, an L/D ratio refers to the ratio of the length L of a segment of the stent to a diameter D of the stent in its expanded state. Although the stent can be made from any of several known shape memory or superelastic biocompatible materials, as should be readily appreciated by the artisan, the stent 100 described herein is preferably comprised of a superelastic alloy such as Nitinol. Most preferably, the stent 100 is made from an alloy comprising about 50.0 percent (as used herein these percentages refer to weight percentages) Ni to about 60 percent Ni, and more preferably about 55.8 percent Ni, with the remainder of the alloy being Ti. Preferably, the stent 100 is designed such that it is superelastic at body temperature, and preferably has an $A_f$ in the range from about twenty-four degrees C to about thirty-seven degrees C. The superelastic design of the stent 100 makes it crush recoverable, which renders the stent useful in any number of vascular devices in different applications.

Stent 100 is a generally tubular member having an open front end 101 and an open back end 102. A longitudinal axis extends therebetween said open front and back ends. In its constrained, state, referring still to FIG. 1, the stent 100 has a first diameter $D_1$ that accommodates insertion of the stent 100 into and navigation through the vasculature of the patient to an intended treatment site. Upon reaching the intended treatment site, the stent 100 is deployed and expands to a second diameter $D_2$, wherein $D_2$ is larger than $D_1$.

Figure 2:
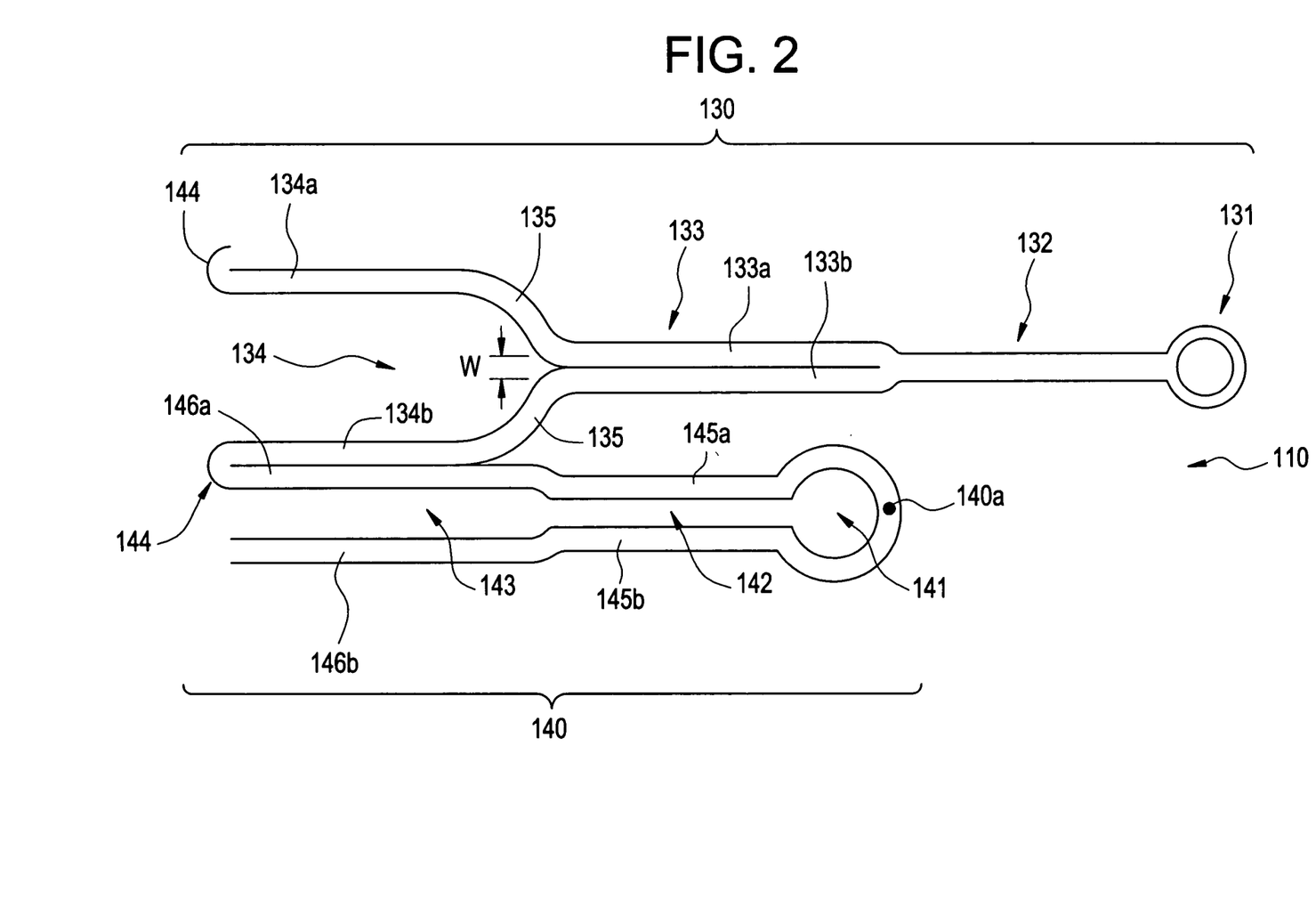
FIG. 2 illustrates one repeating cell of the stent of FIG. 1 according to the invention.

Referring to FIG. 1 and FIG. 2, the stent 100 is further comprised of a series of repeating cells 110. Each cell 110 is radially and circumferentially aligned with adjacent cells 110 within a segment 120, and axially aligned with cells of an axially adjacent segment 120 to comprise a series of axially adjacent segments 120. At least one cell 110 in each segment 120 further comprises a protrusion 130, and at least one cell 110 in each segment 120 further comprises a receptacle 140. Interconnecting the protrusions 130 with the receptacles 140 of an axially adjacent segment 120 forms the stent 100. Preferably, the length L of each segment 120 is such that the L/D ratio is greater than one, using the L and D dimensions of the stent 100 in its expanded state. As shown in FIG. 1, the segments 120 nest, or partially overlap, such that even after deployment and any designed or inadvertent uncoupling of the protrusions from the receptacles due to expansion of the stent, the stent 100 provides enhanced vascular support to the vessel in which the stent is emplaced as certain of the segment overlap is maintained.

Figure 2A:
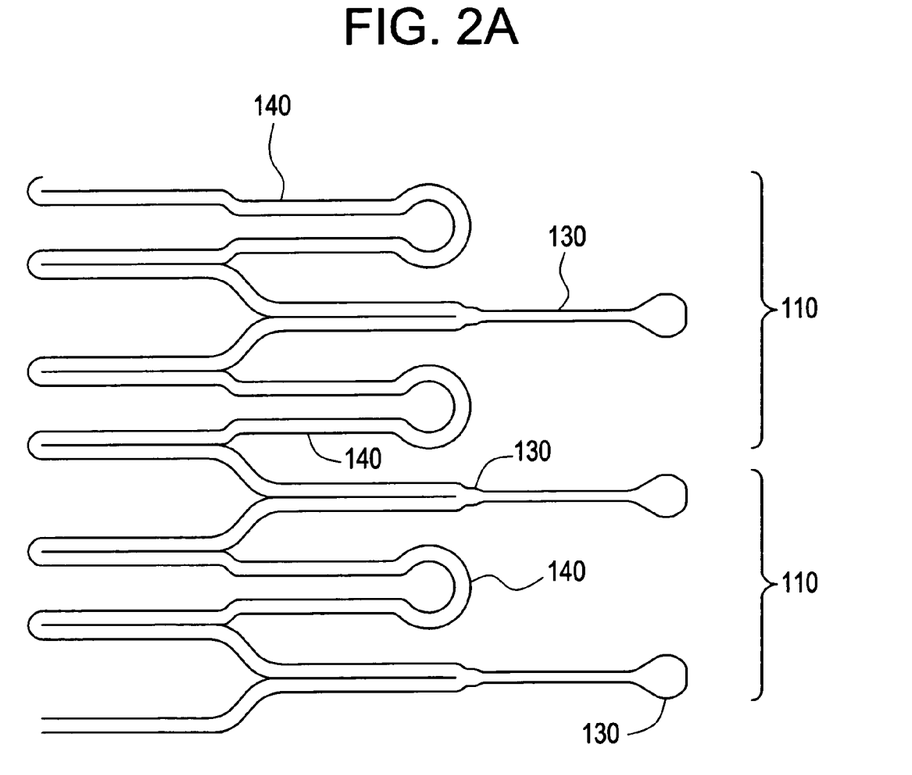
FIG. 2A illustrates another arrangement of a repeating cell according to the invention.

A single cell 110 is shown in more detail in FIG. 2. The cell 110 is thus further comprised of the protrusion 130 and a radially and circumferentially adjacent receptacle 140. Of course, the artisan will appreciate that each cell 110 comprising a segment 120 need not have a protrusion and receptacle, provided that at least one cell 110 from among the cells 110 comprising a segment 120 is comprised of a protrusion 130 and a receptacle 140 in order to render interconnection of axially adjacent stent segments 120 achievable. Of course, the artisan will appreciate that a cell 110 may be comprised of various other configurations of protrusions 130 and receptacles 140. For example, FIG. 2A illustrates a cell 110 comprised of a protrusion 130 flanked by receptacles 140. The protrusions could instead by flanked by non-receptacle strut sections that are longer than, or of equal length as, the length L of the protrusions, provided that the L/D ratio of the protrusions relative to the diameter of the stent is achieved.

Referring again to FIG. 2, the protrusion 130 of each cell 110 is further comprised of an end 131, a single shaft 132, a bi-furcated shaft 133, and a flared base 134. The end 131 extends, typically proximally, from the single shaft 132. The single shaft 132 in turn extends from the bi-furcated shaft 133, wherein the bi-furcated shaft 133 is comprised of generally parallel longitudinal struts 133a, 133b. The longitudinal struts 133a, 133b are spaced closely relative to one another and converge at one end to become the single shaft 132. The longitudinal struts 133a, 133b may be, for example, approximately one laser width (w) apart, or may be other than one laser width (w) apart, particularly where techniques other than, or in addition to, laser cutting is used to form the stent. The bi-furcated shaft 133 in turn extends from the flared base 134, wherein the flared base 134 is comprised of generally parallel longitudinal struts 134a, 134b. The longitudinal struts 134a, 134b taper into shoulders 135, each shoulder 135 converging into a respective one of the longitudinal struts 133a, 133b comprising the bi-furcated shaft 133. Ends 131 of the protrusions may be further comprised of radiopaque materials in order to enhance fluoroscopic, or other, visualization of the device during delivery and emplacement thereof. The radiopaque material is preferably fitted into a portion of the end 131 of the protrusions 130, as by inserting a tantalum marker into the end 131, for example, although other radiopaque materials may be used. Alternatively, the radiopaque material may be integrated with, or coated onto, the end 131 of the protrusion 130.

As shown also in FIG. 2, the receptacle 140 of each cell 110 is further comprised of a first cavity 141, a second cavity 142, and a third cavity 143. The first cavity 141 extends from the second cavity 142, and the second cavity extends from the third cavity 143. A longitudinal strut 140a generally forms the continuous contours of the receptacle 140, wherein the first cavity 141 is comprised of a changeable interior diameter d into which the end 131 of a protusion 130 is received. The second cavity 142 is comprised further of a pair of generally parallel strut sections 145a, 145b, each respectively extending at one end from the first cavity 141 to the third cavity 143 at another end thereof. The second cavity 142 receives the single shaft 132 such that the single shaft 132 is readily restrained therebetween the strut sections 145a, 145b by an angle of the strut sections 145a, 145b relative to the single shaft 132 when the stent 100 is in its constrained state. Expansion of the stent 100 results in expansion of the diameter d of the first cavity 141, and expansion of the angle of the strut sections 145a, 145b of the second cavity 142, thereby enabling axial de-coupling of the end 131 and single shaft 132 of the protrusion 130 from the first cavity 141 and second cavity 142, respectively, of the receptacle 140. The third cavity 143 is further comprised of a pair of longitudinal strut sections 146a, 146b extending, respectively, from the strut sections 145a, 145b of the second cavity 142.

Because the length L of each segment 120 is increased so as preferably to provide a L/D ratio greater than one in the constrained state of the stent, the interlocked protrusions 130 and receptacles 140 of the stent remain interlocked longer during delivery of the stent to an intended treatment site. In this regard, referring still to FIG. 2, expansion of the stent 100 occurs as the stent emerges from a sheathed delivery system. This expansion continues as the sheath of the delivery system is retracted to expose the stent 100. By providing the segment 120 length L of an L/D ratio greater than one, from the end 131 of the protrusion to the edge 144 connecting the longitudinal struts 134a, 134b and 140a, for example, undesirable or premature uncoupling of the interconnected protrusions 130 and receptacles 140 of the adjacent segments 120 is less likely to occur. Undesirable propelling of segments 120 during delivery is also less likely to occur as a result of the L/D ratio being greater than one. The stent 100 thus more readily expands to its memory diameter D2 and preferably seats itself against the vessel wall at the intended treatment site before the protrusions 1.30 of the delivered segment 120 disengages from the receptacle 140. In particular, as the stent 100 expands, the diameter d of the first cavity 141 of the receptacle 141 expands relative to the end 131 of the protrusion received therein, and the angle of the strut sections 145a, 145b expands relative to the single shaft 132 received therein. As a result, the end 131 and single shaft 132 of the protrusion axially disengage from the first cavity 141 and second cavity 142, respectively, of the receptacle 140. Delivery control, positioning and stability of the stent 100 is thus improved, which tends to enhances treatment of the intended site as a result.

Figure 3:
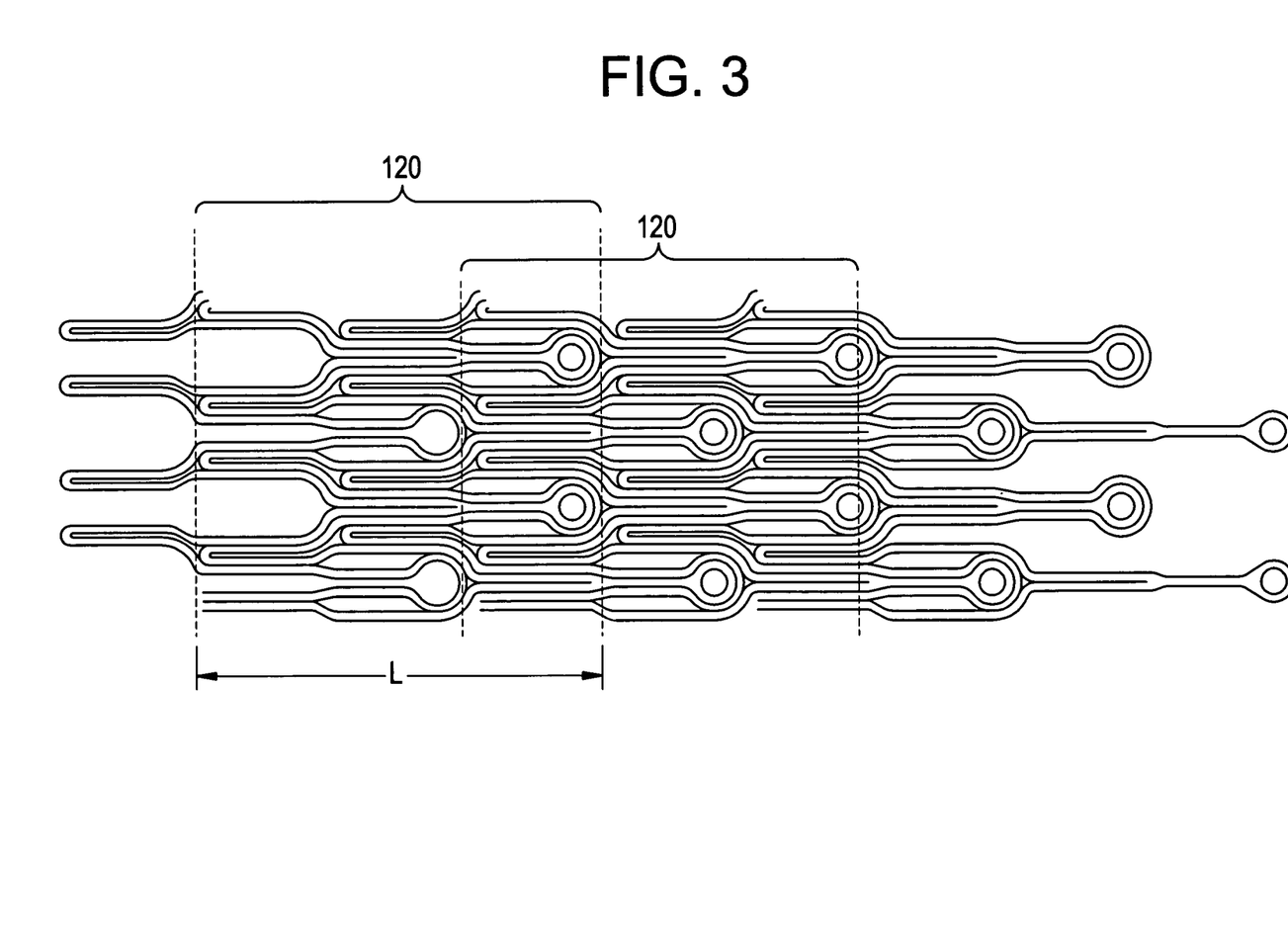
FIG. 3 illustrates a flat projection of a series of interlocking stent segments of the stent of FIG. 1 according to the invention.

FIG. 3 illustrates a flat projection of a series of interlocking segments 120 in their constrained state. Evident in FIG. 3 are the repeating cells 110 that are radially and circumferentially adjacent one another within a segment 120, and that are axially aligned and interconnected with a corresponding cell 110 in an axially adjacent segment 120 so as to comprise the stent 100.

In practice, where a plurality of axially adjacent segments 120 comprised of a plurality of cells 110 comprises the constrained stent 100, the protrusion 130 of at least one cell 110 from one segment 120 is received in the receptacle 140 of the axially adjacent segment 120. More particularly, the end 131 of the protrusion 130 is received in the first cavity 141 of the receptacle, the single shaft 132 of the protrusion is received in the second cavity 142 of the receptacle, and the bi-furcated shaft 133 of the protrusion is received in the third cavity 143 of the receptacle. The constrained stent 100 is thus loaded into a sheathed delivery system similar to as described in co-pending U.S. patent application Ser. No. 10/687,143, filed Oct. 16, 2003, of common assignment herewith, and incorporated herein by reference with respect to the delivery system (FIGS. 10, 11 and 21).

Figure 6:
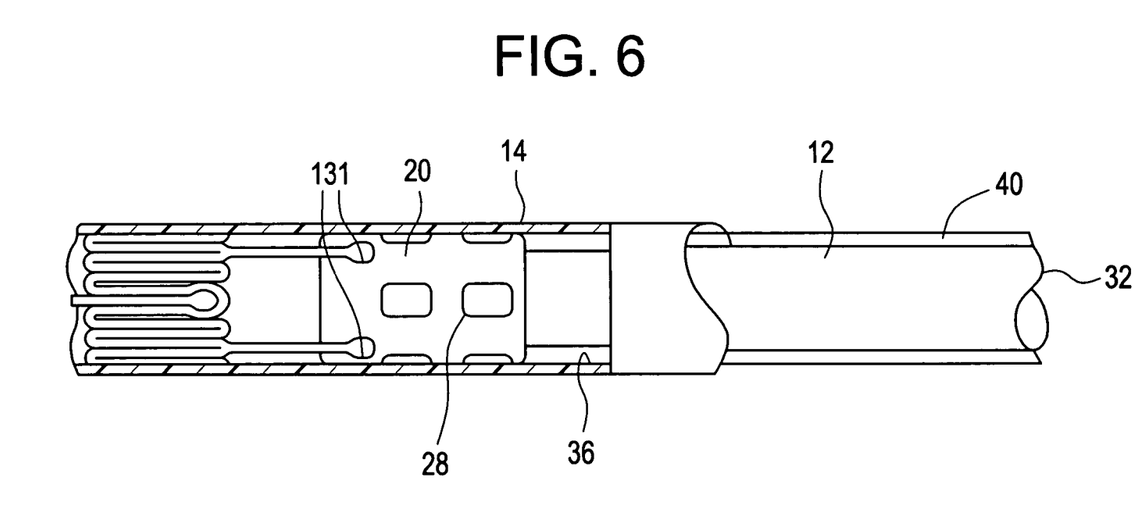
FIG. 6 illustrates aspects of a delivery device corresponding to the various embodiments of the stent according to the invention.

As shown in FIG. 6 herein, the shaft 12 of the delivery system in this case, however, may comprise a collar or modified stop 28 that accommodates the ends 131 of protrusions 130 at the proximal-most end of the stent 100. The collar or modified stop 28 engages the proximal segment 120 of the stent and maintains axial connection therewith until the sheath 14 of the delivery system is retracted over the collar 28 to release the stent segment 120. Optionally, a radial protrusion 40, foam sleeve, or other device, may be provided over the shaft 12 of the delivery system to help minimize unintended circumferential or radial deflections of the ends 131, or other portions, of the protrusions 130 until the sheath 14 is sufficiently retracted to allow each segment 120 to deploy in turn until the stent 100 is fully deployed.

Although described hereinabove is a preferred embodiment of the intraluminal medical device according to the invention, the geometry of the interlocking segments may take many forms other than, or in addition to, that geometry described above. For example, the cell 110 may repeat any number of times radially to form stents of various diameters. The cell 110 may also be altered to provide different, or additional, configurations from the same tubing material from which the stent is laser cut. The cell geometry may be constructed, for example, such that axes of the longitudinal struts comprising the cells 110 are other than parallel with the axis of the tube from which the stent is cut or the vessel in which the stent is emplaced. Further, the length of the cells 110 may be varied, or the number of interconnected axially adjacent stent segments 120 may be varied, to form stents of various overall lengths. Such variations are well within the artisan's understanding and not detailed further herein.

Figure 4:
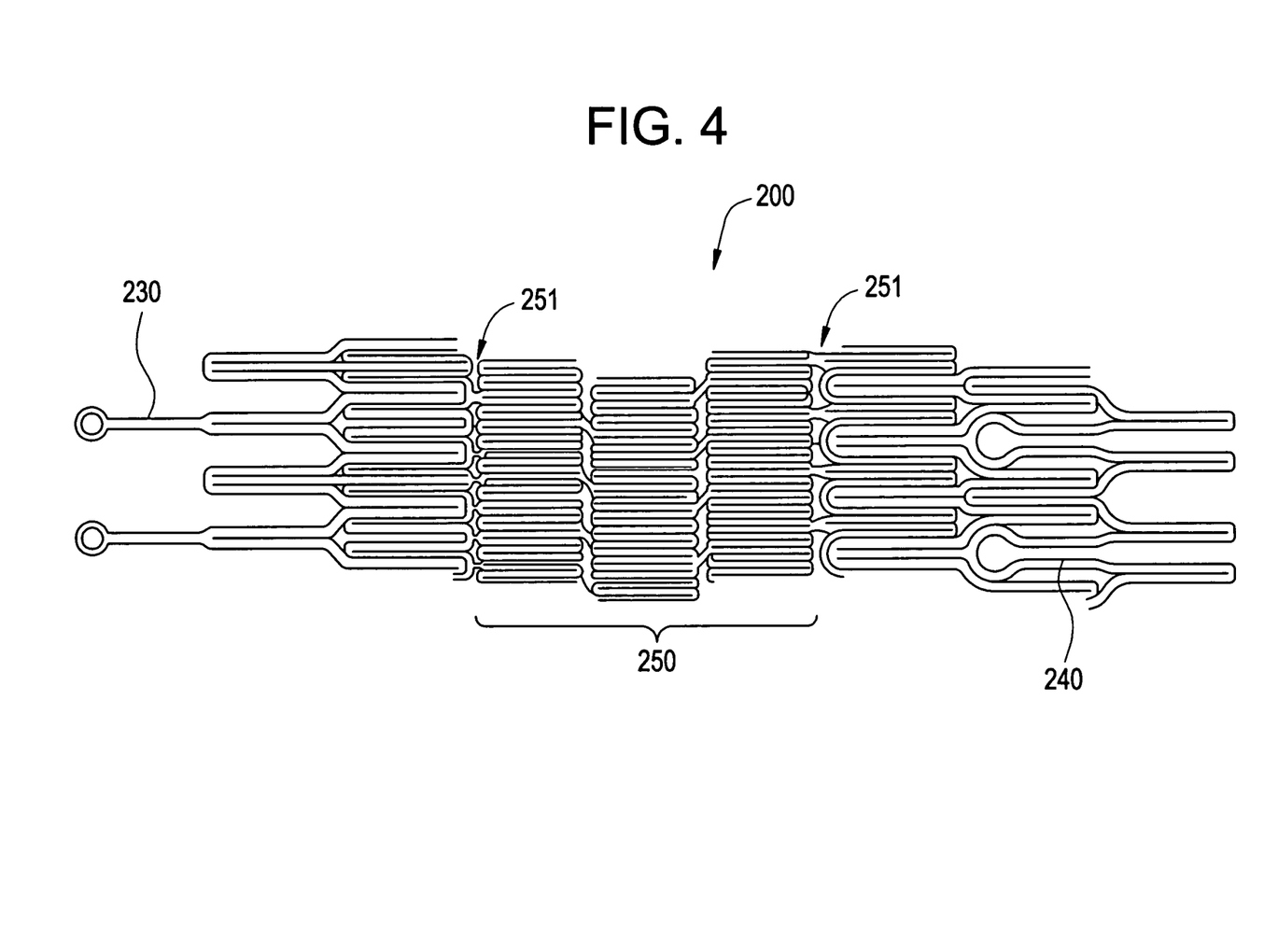
FIG. 4 illustrates a hybrid self-expanding stent according to the invention.

FIG. 4 illustrates a flat projection of a hybrid stent 200 according to the invention. The hybrid stent 200 combines the nestable features of the protrusions 230 and receptacles 240, as otherwise described above using the 100 series reference numerals, together with a plurality of otherwise conventional undulating longitudinal struts 250 interposed between one segment at a proximal end of the stent and one segment at a distal end of the stent. The proximal and distal ends of the stent 200 thus comprise the nestable features of the protrusion 230 and receptacles 240, whereas the plurality of conventional undulating longitudinal struts 250 extend therebetween the proximally and distally located protrusions 230 and receptacles 240 and are integral therewith. The transition areas 251 between these different features, i.e., between the plurality of conventional struts 250 and the proximally and distally located protrusions 230 and receptacles 240, are designed to maximize usage of the tubing from which the hybrid stent 200 is cut.

Figure 5:
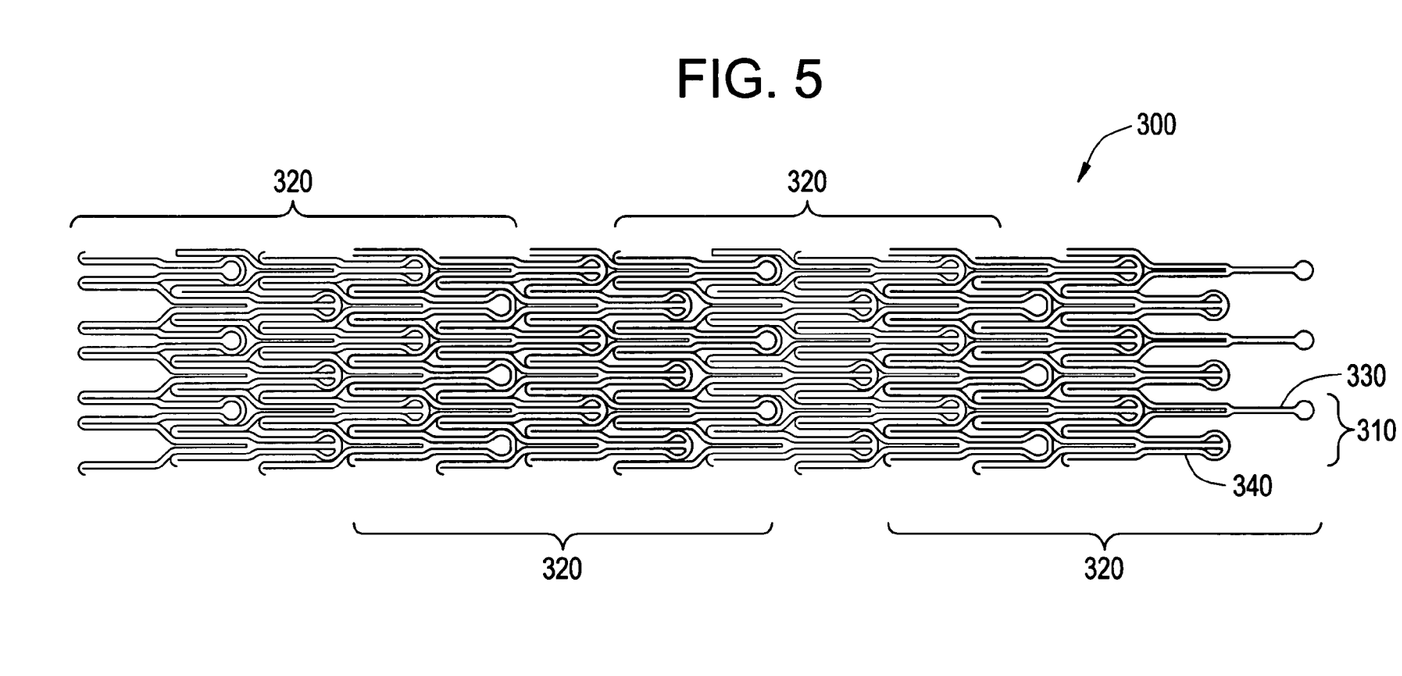
FIG. 5 illustrates another hybrid stent according to the invention.

FIG. 5 illustrates another variation of a hybrid stent 300 according to the invention. The hybrid stent 300 is generally the same as the stent 100 of FIG. 1 except that each segment 320 is comprised of additional radial, circumferentially and axially arranged protrusions and receptacles that are fused together, wherein axially adjacent segments comprise the stent. In other words, each segment 120 of FIG. 1 is comprised of cells 110 having one set of protrusions 130 and receptacles 140, whereas the segments 320 of FIG. 3 is comprised of cells 310 having another set of protrusions 330 and receptacles 340 axially aligned and fused together to comprise a single segment 320. As before, the stent 300 is thus comprised of a series of axially interconnected segments 320.

Although not shown, a balloon expandable stent, rather than the self-expanding stents described above, could instead comprise the intraluminal medical device according to the invention. The balloon expandable stent is preferably comprised of stainless steel, cobalt alloy, or other alloy conventional in the art. The balloon expandable stent is otherwise comprised of the features described above with respect to the preferred embodiment of the self-expandable stent 100 wherein the cells comprising a segment are radially and circumferentially aligned relative to one another within a segment, and are axially aligned with axially adjacent segments to comprise the stent. Delivery of the balloon expandable stent would likewise comply with that described above, except that expansion of the balloon expandable stent would occur via inflation of a balloon from the interior of the constrained balloon expandable stent in conventional fashion. Because the axially adjacent stent segments are interconnected in the constrained state during delivery of the balloon expandable stent, stable and controllable delivery of the stent is achieved. Likewise, because the axially adjacent segments remain at least partially nested after expansion and full deployment of the stent via the balloon, enhanced vascular support to the vessel within which the stent is emplaced is achieved. As before, ends of the protrusions may be comprised of radiopaque materials so as to comprise markers to enhance fluoroscopic, or other, visualization. The markers may be separately inserted into the ends of the protrusions, or may be integral with, or coated thereon the ends of the protrusions.

The various exemplary embodiments of the invention as described hereinabove do not limit different embodiments of the systems and methods of the invention. The material described herein is not limited to the materials, designs or shapes referenced herein for illustrative purposes only, and may comprise various other materials, designs or shapes suitable for the systems and methods described herein, as should be appreciated by the artisan.

While there has been shown and described what is considered to be preferred embodiments of the invention, it will, of course, be understood that various modifications and changes in form or detail could readily be made without departing from the spirit or scope of the invention. It is therefore intended that the invention be not limited to the exact forms described and illustrated herein, but should be construed to cover all modifications that may fall within the scope of the appended claims.

What is claimed is:

1. A self-expanding stent, comprising: a plurality of non-connected, axially adjacent segments each having a length; a series of radially and circumferentially adjacent repeating cells comprising each segment, wherein each cell is an open structure; a predetermined number of protrusions extending from each segment, each protrusion comprising an end, a single shaft, a bifurcated shaft formed from parallel struts and spaced apart a first predetermined distance and a flared base formed from parallel struts spaced apart a second predetermined distance greater than the first predetermined distance and connected to the parallel struts of the bifurcated shaft via shoulders; a predetermined number of receptacles provided in each segment and aligned to receive a corresponding protrusion from one of the axially adjacent segments, each receptacle comprising a first cavity for receiving an end of a protrusion, the first cavity being a circular ring configuration and having a changeable diameter, a second cavity comprising struts configured to create an angle of convergence for retaining the single shaft when the stent is unexpanded and a third cavity configured to receive the bifurcated shaft, the first cavity comprising an opening wherein it joins the second cavity, the opening being equal to the distance between the struts forming the second cavity, the third cavity being formed from substantially parallel struts that have ends that neck down to the struts of the second cavity, the struts of the third cavity being connected to the struts of the flared base, the first cavity having a greater circumferential dimension than both the second and third cavities; wherein the stent comprises a length of segment to expanded stent diameter ratio, L/D, of greater than one in the constrained state such that the predetermined number of protrusions of the segments interlock and remain engaged with the corresponding receptacles of one of the axially adjacent segments during delivery of the stent and a portion of the length of each segment overlaps with a portion of the length of one or more adjacent segments after delivery.

2. The self-expanding stent of claim 1, wherein each segment is of an expanded length greater than an expanded diameter of the stent such that a length to diameter ratio is greater than one.

3. The self-expanding stent of claim 2, wherein the predetermined number of protrusions disengage from the corresponding predetermined number of receptacles after delivery and full deployment of the stent is effected.

4. The self-expanding stent of claim 1, wherein each segment is of an expanded length less than or equal to an expanded diameter of the stent such that a length to diameter ratio is less than or equal to one.

5. The self-expanding stent of claim 1, wherein ends of the protrusions are comprised of radiopaque material.

6. The self-expanding stent of claim 5, wherein the radiopaque material is inserted into the end of at least one of the protrusions.

7. The self-expanding stent of claim 5, wherein the radiopaque material is integral with, or coated thereon, the end of at least one of the protrusions.

8. The self-expanding stent of claim 1, wherein the stent is formed from a single tube comprised of one of shape memory or superelastic materials.

9. The self-expanding stent of claim 1, wherein the stent is comprised at least partially of Nitinol.

10. The self-expanding stent of claim 1 wherein the predetermined number of protrusions of each segment is at least one and the predetermined number of receptacles of each segment is at least one such that at least one protrusion and at least one receptacle is provided in alignment relative to one another on one of the axially adjacent segments.

11. The self-expanding stent of claim 1, wherein the predetermined number of protrusions disengage from the corresponding predetermined number of receptacles after delivery and full deployment of the stent is effected.

12. The self-expanding stent of claim 1, wherein a plurality of undulating longitudinal struts are interposed between one of the segments at a proximal end of the stent and one of the segments at a distal end of the stent so as to form a hybrid stent.

13. The self-expanding stent of claim 1, wherein each segment is further comprised of at least one set of radially, circumferentially and axially aligned receptacles and protrusions that are fused together.

14. The self-expanding stent of claim 1, wherein each cell is comprised of at least two protrusions flanking at least one receptacle.

15. The stent of claim 14, wherein the balloon expandable stent is comprised of at least one of stainless steel or cobalt alloy.

16. The stent of claim 1, wherein the stent is instead a balloon expandable stent.

* * * * *